United States Patent [19]

Dettmar

[11] Patent Number: 4,705,683
[45] Date of Patent: Nov. 10, 1987

[54] PHARMACEUTICAL COMPOSITIONS

[75] Inventor: Peter W. Dettmar, Welwick, Great Britain

[73] Assignee: Reckitt & Colman Products Limited, Great Britain

[21] Appl. No.: 832,995

[22] Filed: Feb. 26, 1986

[30] Foreign Application Priority Data

Mar. 1, 1985 [GB] United Kingdom ................ 8505298
Mar. 16, 1985 [GB] United Kingdom ................ 8506855

[51] Int. Cl.$^4$ ..................... A61K 31/78; A61K 31/415
[52] U.S. Cl. ....................................... 424/81; 514/396
[58] Field of Search .......................................... 424/81

[56] References Cited

U.S. PATENT DOCUMENTS 4,140,760  2/1979  Withington ........................... 424/81
4,273,761  1/1981  Matsuda et al. ...................... 424/81

OTHER PUBLICATIONS

A. Watson, British Society of Gastroenterology, 25, pp. A553–A554, (1985).
Bennett et al., The British Society of Gastroenterology, 25, p. A556, (1984).

*Primary Examiner*—Stanley J. Friedman
*Attorney, Agent, or Firm*—Bacon and Thomas

[57] ABSTRACT

Pharmaceutical compositions comprising mixtures of a histamine $H_2$-receptor antagonist such as cimetidine or ranitidine and sodium polyacrylate in a specified range of ratios have been found to exhibit synergistic effects in an in vivo test model for anti-ulcer or mucosal-protecting agents. Pharmaceutical compositions comprising mixtures of a histamine $H_2$-receptor antagonist such as cimetidine or ranitidine and sodium polyacrylate in the range of ratios are described for use in the treatment of gastritis or of gastro-duodenal ulcers. In a modification in the mixtures the sodium polyacrylate may be replaced wholly or in part by potassium or ammonium polyacrylate.

13 Claims, No Drawings

PHARMACEUTICAL COMPOSITIONS

This invention relates to pharmaceutical compositions and in particular to compositions for the treatment of gastritis and gastro-duodenal ulcers.

In animal studies cimetidine and rantidine have been shown to act as specific competitive histamine $H_2$-receptor antagonists which effectively inhibit gastric acid secretion. Cimetidine and ranitidine are the only $H_2$-receptor antagonists that are currently available for clinical use and are now widely accepted as the first-line agents for the management of acute peptic ulceration and also for maintenance phophylactic treatment, more recently these agents have been used for the treatment of gastritis and oesophagitis.

Sodium polyacrylate has been suggested for use in the treatment of peptic ulcers. British Pat. No. 1435630 describes a solid antipeptic ulcer composition comprising sodium polyacrylate having an intrinsic viscosity of 0.3 or more and a pharmaceutically inert solid carrier. British Pat. No. 1538352 describes an improved composition which comprises granules of polyacrylic alkali metal salt coated with a water-insoluble but water permeable coating agent. Suitable polyacrylic alkali metal salts are stated to include sodium polyacrylate of molecular weight 3,000,000 to 8,000,000. The only specific sodium polyacrylate mentioned is one of molecular weight about 3,400,000.

We have carried out investigations into the mucosal-protective properties of specific competitive histamine $H_2$-receptor antagonists namely cimetidine and ranitidine and various acid polymers of natural and synthetic origin. We have surprisingly discovered that there is a synergistic effect when the histamine $H_2$-receptor antagonist and sodium polyacrylate are mixed in certain proportions. We have also found that the presence of sodium alginate reduces the binding properties of sodium polyacrylate to the gastric mucosa.

According to this invention there is provided a pharmaceutical composition comprising a histamine $H_2$-receptor antagonist and sodium polyacrylate in a weight ratio of from 10:1 to 1:10, and preferably from 5:1 to 1:5.

As used herein "sodium polyacrylate" denotes the sodium salt of polyacrylic acid which may be linear or crosslinked. Examples of commercial grades of linear polyacrylates are Carbopol 907 (free acid form B.F. Groodrich) and Aronvis (sodium salt Nihon Junyaku). Carbopol 907 is a linear polyacrylate having a molecular weight of approximately 450,000. Examples of commercial grades of cross-linked sodium polyacrylates are Rheogic 252L, Rheogic 250 H (Nihon Junyaku), and Hostacerin PN73 (Hoescht U.K. Ltd.) A preferred crosslinked polyacrylate is one of the carbomer range (free acid form).

In an aspect of this invention there is provided a pharmaceutical composition comprising a histamine $H_2$-receptor antagonist and sodium polyacrylate in a weight ratio of from 1:1 to 1:10, and preferably from 1:1 to 1:5.

In a modification of the invention the sodium polyacrylate may be replaced wholly or in part by potassium or ammonium polyacrylate or mixtures thereof.

In the compositions preferably the histamine $H_2$-receptor antagonist is cimetidine or ranitidine. Preferably the sodium polyacrylate is carbomer sodium.

Carbomer is described in the British Pharmacopeia and the United States National Formulary as being a synthetic high molecular weight cross-linked polymer of acrylic acid containing 56 to 68% of carboxylic acid groups. The British Pharmacopeia specifies cross-linking with allylsucrose. Carbomer is used in the form of neutralised gel as a suspending agent in pharmaceutical preparations for internal and external uses. U.S. Pat. No. 2,909,462 describes the use as a bulk laxative of a colloidally water-soluble polymer of acrylic acid cross-linked with from about 0.75% to 2.0% of polyallyl sucrose.

Examples of suitable commercial grades of carbomer are those sold by B. F. Goodrich under the Registered Trade Marks Carbopol 910, 934, 934P, 940 and 941. These carbomer grades have molecular weights between approximately 750,000 and 4,000,000. Other examples are those sold by Nihon Junyaku as Junlon PW110, Junlon PW150 and Junlon PW111, and Acrisint 400 (Sigma, Italy). In the compositions of the present invention the preferred material is carbomer 934P, having a molecular weight of approximately 3,000,000, a commercial grade being Carbopol 934P. (See USAN and the USP dictionary of drug names, USAN 1984 page 89).

The compositions of the invention are for oral administration and may be in the form of aqueous compositions having a pH of between 7 and 9. Where the polyacrylate used is in the acid form in its converted to the appropriate salt form during the manufacturing process.

The invention also includes the use of a histamine $H_2$-receptor antagonist and sodium polyacrylate in a weight ratio of from 10:1 to 1:10, preferably in a ratio of 5:1 to 1:5 and most preferably in the ratio 1:1 to 1:5 in the treatment of gastritis or gastro-duodenal ulcers.

In a further aspect of the invention provides a method of treating gastritis or gastro-duodenal ulcers which comprises administering to a subject an orally effective amount of a pharmaceutical composition comprising a histamine $H_2$-receptor antagonist and sodium polyacrylate in a weight ratio of from 10:1 to 1:10, preferably in the ratio of 5:1 to 1:5 and most preferably from 1:1 to 1:5.

In the treatment of gastritis or gastro-duodenal ulcers the normal unit dosage of the histamine $H_2$-receptor antagonist will be in the case of cimetidine in the range 800 to 10 mg and for ranitidine in the range 150 to 5 mg and that of the polyacrylate in the range 300 to 10 mg provided that the weight ratio of the histamine $H_2$-receptor antagonist to the polyacrylate falls within the range of 10:1 to 1:10, preferably in the range of 5:1 to 1:5 and most preferably in the range 1:1 to 1:5.

Because of the synergistic effecte between the histamine $H_2$-receptor antagonist and polyacrylate the present compositions afford the possibility of lower doses of the histamine $H_2$-receptor antagonist being used with a resultant reduction in side effects.

The compositions may also include an antacid. Suitable materials include sodium bicarbonate, calcium carbonate, aluminium hydroxide and mixtures thereof. Use of these materials, in particular sodium bicarbonate, also results in a reduction in the viscosity of the liquid compositions, thereby providing some degree of viscosity control in the design of readily pourable liquid preparations.

With aqueous compositions, which are susceptible to contamination and subsequent deterioration by microorganisms it is preferable to include a preservative. A suitable system is a combination of methyl and propyl-p-hydroxy benzoates (methyl paraben or propyl paraben) or their sodium salts.

The pharmaceutical compositions of the present invention may also include one or more of a colouring, sweetening or flavouring agent.

The invention is illustrated by the following Examples.

EXAMPLES 1 TO 4

Liquid preparations were prepared having the following formulations:

|  | Example No. | | | | |
|---|---|---|---|---|---|
|  | 1 | 2 | 3 | 4 | |
| Carbopol 934P | 1.0 | 1.0 | 1.0 | 1.0 | g |
| Cimetidine | 0.5 | 0.33 | 0.25 | 0.2 | g |
| Sodium bicarbonate | 1.0 | 1.0 | 1.0 | 1.0 | g |
| Calcium carbonate | 1.0 | 1.0 | 1.0 | 1.0 | g |
| Methyl paraben, sodium | 0.15 | 0.15 | 0.15 | 0.15 | g |
| Propyl paraben, sodium | 0.022 | 0.022 | 0.022 | 0.022 | g |
| Sodium hydroxide | qs | qs | qs | qs | |
| Water | to 100 | 100 | 100 | 100 | ml |
| pH | 8.0 | 8.1 | 8.0 | 8.1 | |

The Carbopol was dispersed, with agitation, in about 60 ml water, and aqueous sodium hydroxide added to adjust the pH to about 6.5. The cimetidine, sodium bicarbonate, methyl paraben sodium and propyl paraben sodium were dissolved with agitation and heating in about 30 ml water followed by the addition of calcium carbonate. The resultant mixture was added to the Carbopol gel followed by additional water to make up to a volume of 100 ml.

EXAMPLES 5 TO 8

Solid preparations in the form of capsules were prepared from the following mixes:

|  | Example No. | | | | |
|---|---|---|---|---|---|
|  | 5 | 6 | 7 | 8 | |
| Carbopol 934P sodium salt | 20 | 20 | 20 | 20 | g |
| Cimetidine | 20 | 10 | 6.6 | 4 | g |
| Calcium carbonate | 20 | 20 | 20 | 20 | g |
| Lactose | 40 | 50 | 53.4 | 56 | g |

Carbopol 934P sodium salt was prepared by dispersing 1 kg Carbopol 934P in a solution of 400 g sodium hydroxide in 3.6 kg anhydrous methanol. The salt was collected by filtration, dried and comminuted.

The formulation ingredients were blended and well mixed to form a uniform mix. 500 mg aliquots were taken and filled into size 00 hard gelatine capsules. For example 5 the 500 mg aliquot contained 100 mg Carbopol 934P sodium, 100 mg cimetidine, 100 mg calcium carbonate and 200 mg lactose.

EXAMPLES 9 TO 10

Liquid preparations were prepared having the following formulations:

|  | Example No. | | |
|---|---|---|---|
|  | 9 | 10 | |
| Carbopol 934P | 1.0 | 1.0 | g |
| Ranitidine | 0.5 | 0.2 | g |
| Sodium bicarbonate | 1.0 | 1.0 | g |
| Calcium carbonate | 1.0 | 1.0 | g |

-continued

|  | Example No. | | |
|---|---|---|---|
|  | 9 | 10 | |
| Methyl paraben, sodium | 0.15 | 0.15 | g |
| Propyl paraben, sodium | 0.022 | 0.022 | g |
| Sodium hydroxide | qs | qs | |
| Water | to 100 | 100 | ml |
| pH | 8.1 | 8.0 | |

The Carbopol, sodium bicarbonate, calcium carbonate, methyl paraben sodium and proply paraben sodium were dispersed with rapid agitation in about 70 ml water. The ranitidine (as a solution of the hydrochloride in 20 ml water) was added with rapid stirring followed by the addition of aqueous sodium hydroxide to adjust the pH and additional water to make up to a volume of 100 ml.

EXAMPLES 11 TO 14

Solid preparations in the form of capsules were prepared from the following mixes:

|  | Example No. | | | | |
|---|---|---|---|---|---|
|  | 11 | 12 | 13 | 14 | |
| Carbopol 934 sodium salt | 10 | 20 | 20 | 20 | g |
| Ranitidine | 10 | 10 | 6.6 | 4 | g |
| Calcium carbonate | 20 | 20 | 20 | 20 | g |
| Lactose | 60 | 50 | 53.4 | 56 | g | and filled as 500 mg aliquots into size 00 hard gelatine capsules by the method as described in Examples 5 to 8.

EXAMPLE 15

A solid preparation in the form of capsules was prepared from the following mix:

| Carbopol 934P sodium salt | 8 g |
|---|---|
| Cimetidine | 40 g |
| Calcium carbonate | 16 g |
| Lactose | 36 g | and filled as 500 mg aliquots into size 00 hard gelatine capsules by the method as described in Examples 5 to 8, each 500 mg aliquot containing 40 mg Carbopol 934P sodium salt, 200 mg cimetidine, 80 mg calcium carbonate and 180 mg lactose.

EXAMPLE 16

A liquid preparation was prepared having the following composition

|  | % w/w |
|---|---|
| Carbopol 934P | 1.00 |
| Cimetidine | 1.00 |
| Sodium bicarbonate | 1.00 |
| Calcium carbonate | 1.00 |
| Methyl paraben | 0.41 |
| Propyl paraben | 0.11 |
| Monammonium glycerrhizinate | 0.50 |
| Glycerol | 5.00 |
| Flavouring/sweetening agent | 0.051 |
| Sodium hydroxide | qs |
| Water | to 100 |
| pH | 8.1 |

The Carbopol was dispersed, with agitation, in about 60% of the water and aqueous sodium hydroxide added to adjust the pH to about 6.0. The sodium bicarbonate, calcium carbonate, methyl paraben, propyl paraben and sweetening agent were mixed with about 30% of the water. The resultant mixture was added to the Carbopol gel followed by the addition of the cimetidine and the monoammonium glycerrhizinate (dissolved in warm glycerol), made upto volume with additional water and homogenised until smooth.

EXAMPLE 17

The liquid preparation of Example 1 was varied by using potassium hydroxide in place of the sodium hydroxide.

EXAMPLE 18

The liquid preparation of Example 1 was varied by using ammoniun hydroxide in place of the sodium hydroxide.

The pharmaceutical properties of the compositions of the invention have been evaluated in two in vivo rat models.

The anti-ulcer or mucosal-protecting properties were determined in the ethanol-induced gastric necrosis test by a method based on that of Robert A., Nezamis J. E., Lancaster C. and Hanchar A. J., Gastroenterology 77, 433, (1979).

In the test method male Sprague-Dawley rats (150-170 g) were housed singly and fasted for 18 hours and deprived of water for 4 hours prior to the treatment. Drug or drug vehicle was administered orally (n=10 per group) in a dose volume of 5 ml/kg. Thirty minutes later the rats were dosed orally with 80% ethanol (in a dose volume of 5 ml/kg). One hour later the rats were killed by cervical dislocation. The abdomen was opened immediately and the stomach removed. The stomach was opened along the greater curvature and the mucosa was examined by an observer who was unaware of the treatment give. The lesions were measured in millimeters in a systematic manner, their length recorded, and the total lesion length per stomach was determined. The code was broken after all the stomachs had been examined and the severity of the lesion damage was expressed as the mean total lesion length (±SEM) per group of rats. Statistical analysis of the data was performed using Student's 't' test for unpaired data. A pretreatment effect was considered significant if the p value was less than 0.05. The control vehicle treated group mean was compared to that of the drug treated group and the percentage protection from the lesion damage caused by ethanol was determined.

The ability of the compositions to bind (adhere) to the rat gastric mucosa was determined by a method based on that of Green A. P., Lander J. E. and Turner D. H., J. Pharm. Pharmacol. 33, 348, (1981). The method employs a cationic dye, alcian blue, that binds to acidic mucopolysaccharides present in gastric mucus. In vitro, this dye gives a positive reaction with polysaccharides e.g. k-carrageanan, alginate, carboxymethyl cellulose and xanthan, and polyacrylates e.g. carbomer.

In the test method male Sprague-Dawley rats (130-150 g) were housed singly and fasted overnight for 18 hours before treatment. Following treatment (administered orally in a dose volume of 5 ml/kg) the rats (n=10 per group) were left for a further 60 minutes before being killed by cervical dislocation. The abdomen was opened immediately, the stomach was dissected out, freed of any connective tissue and opened along the greater curvature. The stomachs were gently washed under slightly running water and placed into 10 ml of ice-cold 0.25M sucrose solution. The stomachs in the sucrose solution were then weighed on an electronic balance (Sartorius 1212 MP) and the approximate wet weight of each stomach was determined. The stomachs were removed from the sucrose solution and lightly shaken with forceps to remove excess sucrose. The washed stomachs were then incubated in 10 ml of freshly prepared Alcian Blue 8GX (Aldrich Chemical) dye solution (1 mg/ml), in 0.15M sucrose buffered with 0.05M sodium acetate that had been adjusted to pH 5.8 with HCl, for two hours at room temperature with an occasional shake. The stomachs (now blue) were washed for 10 minutes with 10 ml 0.25M sucrose solution (2x), lightly shaken with forceps to remove excess sucrose and placed in 15 ml of 0.5M magnesium chloride solution for a further two hours at room temperature, shaken occasionally, and removed. The blue magnesium chloride solution was shaken for ~30 seconds with ~3 ml diethyl ether (2x). The optical density of the aqueous layer was measured using disposable cuvettes (4 ml capacity, 1 cm light path) on a Cecil 595 dual beam spectrophotometer at 605 nm. The blank used to compare all the samples (Reference cuvette) was magnesium chloride solution. The results are expressed in optical density units per g tissue weight. Statistical analysis of the data was performed using Student's 't' test for unpaired data. A pretreatment effect was considered significant if the p value was less than 0.05. The percentage difference between the control and test groups was also determined.

Table 1 presents test data for compositions having pH 8.0 containing Carbopol 934P (sodium salt) in the rat ethanol-necrosis test.

TABLE 1

| Treatment (dose %) Carbopol 934P | % Protection | p values |
| --- | --- | --- |
| 0.2 | 2.8 | NS |
| 0.4 | 2.9 | NS |
| 0.5 | 25.8 | NS |
| 0.6 | 16.7 | NS |
| 1.0 | 39.1 | <0.02 |
| 2.0 | 34.5 | <0.05 |

Table 2 presents test data for compositions having pH 8.0 containing Carbopol 934P (sodium salt) in the rat gastric binding test. Table 3 shows the time course of binding with a 1% concentration of Carbopol 934P (sodium salt, pH 8.0) in this test.

TABLE 2

| Treatment (dose %) Carbopol 934P | % Increase in binding | p values |
| --- | --- | --- |
| 0.1 | 11.5 | NS |
| 0.2 | 18.8 | <0.05 |
| 0.5 | 75.2 | <0.001 |
| 1.0 | 118.9 | <0.001 |

TABLE 3

| Time post dose (h) | % Increase in binding | p values |
| --- | --- | --- |
| 0.5 | 109.5 | <0.001 |
| 1 | 118.9 | <0.001 |
| 2 | 58.1 | <0.001 |
| 3 | 65.0 | <0.001 |
| 4 | 36.2 | <0.01 |
| 5 | 36.3 | <0.01 |

TABLE 3-continued

| Time post dose (h) | % Increase in binding | p values |
|---|---|---|
| 6 | 6.0 | NS |

From Table 1 it can be seen that Carbopol 934P (sodium salt) possessed only weak mucosal protective activity (39.1% protection, p<0.01 at 1% dose level) but at this dose level is readily bound to the rat gastric mucosal surface (see Table 2). From Table 3 it can be seen that at a dose level of 1% of the binding persisted for up to 5 hours.

Table 4 presents test data for compositions having pH 8.0 containing cimetidine in the rat ethanol-necrosis test.

TABLE 4

| Treatment (dose %) Cimetidine | % Protection | p values |
|---|---|---|
| 0.6 | 3.1 | NS |
| 2.0 | 9.9 | NS |
| 4.0 | 7.2 | NS |
| 6.0 | 39.0 | <0.02 |
| 10.0 | 75.1 | <0.001 |

From Table 4 it can be seen that cimetidine possessed good mucosal protective activity at the 10% dose level.

Table 5 presents test data for compositions having pH 7.5 to 8.1 containing Carbopol 934P (sodium salt) and varying amounts of cimetidine in the rat ethanol-necrosis test.

TABLE 5

| Treatment (Dose %) Carbopol 934P + Cimetidine | | % Protection | p value |
|---|---|---|---|
| 0.6 | 0.06 | 12.2 | NS |
| 0.6 | 0.12 | 44.1 | <0.05 |
| 0.6 | 0.2 | 54.1 | <0.05 |
| 0.6 | 0.3 | 64.5 | <0.01 |
| 0.6 | 0.6 | 67.9 | <0.01 |
| 0.6 | 1.0 | 74.4 | <0.001 |
| 0.6 | 2.0 | 68.9 | <0.001 |
| 0.6 | 3.0 | 72.0 | <0.001 |
| 0.3 | 3.0 | 53.1 | <0.05 |

From Table 5 it can be seen that when an inactive dose of Carbopol 934P (0.6) was combined with an inactive dose of cimetidine (0.6) significant protection (67.9%) was produced i.e. synergism was exhibited.

Table 6 presents test data for compositions having pH 7.6 to 7.9 containing ranitidine in the rat ethanol-necrosis test.

TABLE 6

| Treatment (Dose %) Ranitidine | % Protection | p Value |
|---|---|---|
| 0.06 | 0 | NS |
| 0.2 | 0 | NS |
| 0.6 | 15.1 | NS |
| 1.0 | 19.1 | NS |
| 2.0 | 43.8 | <0.05 |

From Table 6 it can be seen that ranitidine possessed weak protective activity at the 2.0% dose level.

Table 7 presents test data for compositions having pH 7.8 to 8.3 containing Carbopol 934P (sodium salt) and varying amounts of ranitidine in the rat ethanol-necrosis test.

TABLE 7

| Treatment (Dose %) Carbopol 934P + Ranitidine | | % Protection | p value |
|---|---|---|---|
| 0.6 | 0.06 | 27.1 | <0.05 |
| 0.6 | 0.12 | 30.5 | NS |
| 0.6 | 0.3 | 45.2 | <0.05 |
| 0.6 | 0.6 | 69.9 | <0.05 |
| 0.2 | 1.0 | 38.3 | NS |
| 0.1 | 1.0 | 57.2 | <0.01 |

From Table 7 it can be seen that when an inactive dose of Carbopol 934P (0.6) was combined with an inactive dose of ranitidine (0.6) significant protection (69.9%) was produced i.e. synergism was exhibited.

Investigations were carried out using the above described alcian blue test to determine the effect of sodium alginate on the binding of sodium polyacrylate to the rat gastric mucosa. Table 8 presents data for compositions having ph 8.0 containing Carbopol 934P (sodium salt) or sodium alginate alone and in combination.

TABLE 8

| Treatment | dose % | % increase in binding alone | combination |
|---|---|---|---|
| Carbopol 934P | 1.0 | 118.9 (P < 0.001) | 0.0 |
| Alginate | 6.0 | 8.7 (NS) | |

From Table 8 it can be seen that the binding of sodium polyacrylate was completely inhibited in the presence of the sodium alginate.

Table 9 represents test data obtained with Examples in the rat ethanol necrosis test.

TABLE 9

| Treatment | % Protection | p value |
|---|---|---|
| Example 1 | 45.4 | <0.05 |
| Example 2 | 48.5 | <0.05 |
| Example 4 | 54.8 | <0.05 |
| Example 9 | 46.4 | <0.05 |
| Example 10 | 59.6 | <0.02 |
| Example 16 | 66.0 | <0.01 |

It is to be understood that the compositions of the present invention are preferably substantially free of sodium alginate.

We claim:

1. A pharmaceutical composition comprising a histamine $H_2$-receptor antagonist and a polyacrylate selected from the group consisting of sodium, potassium and ammonium polyacrylates or mixtures thereof having molecular weights between approximately 450,000 and approximately 4,000,000 in a weight ratio of 5:1 to 1:5.

2. A pharmaceutical composition as claimed in claim 1 comprising a histamine $H_2$-receptor antagonist and sodium polyacrylate in a weight ratio of from 1:1 to 1:5.

3. A pharmaceutical composition as claimed in claim 1 wherein the histamine $H_2$-receptor antagonist is cimetidine or ranitidine.

4. A pharmaceutical composition as claimed in claim 1 wherein the polyacrylate is carbomer.

5. A pharmaceutical composition as claimed in claim 4 wherein the carbomer is a polymer of acrylic acid cross-linked with allylsucrose having a molecular weight of about 3,000,000.

6. A pharmaceutical composition as claimed in claim 1 which further includes an antacid.

7. A pharmaceutical composition as claimed in claim 1 in the form of an aqueous composition having a pH of between 7 and 9.

8. A pharmaceutical composition as claimed in claim 1 substantially free of sodium alginate.

9. A pharmaceutical composition as claimed in claim 1 wherein said polyacrylate is sodium polyacrylate.

10. A method of treating gastritis or gastro-duodenal ulcers which comprises administration to a patient an orally effective amount of a pharmaceutical composition comprising a histamine $H_2$-receptor antagonist and a polyacrylate selected from the group consisting of sodium, potassium and ammonium polyacrylates or mixtures thereof having molecular weights between approximately 450,000 and approximately 4,000,000 in a weight ratio of from 5:1 to 1:5.

11. A method of treating gastritis or gastro-duodenal ulcers as claimed in claim 10 wherein the ratio is between 5:1 to 1:5.

12. A method of treating gastritis or gastro-duodenal ulcers as claimed in claim 10 wherein said pharmaceutical composition comprises a histamine $H_2$-receptor and sodium polyacrylate in a weight ratio of from 1:1 to 1:5.

13. A method of treating gastritis or gastro-duodenal ulcers as claimed in claim 10 wherein said polyacrylate is sodium polyacrylate.

* * * * *